(12) United States Patent
Drasler et al.

(10) Patent No.: US 9,186,094 B2
(45) Date of Patent: Nov. 17, 2015

(54) ELLIPTICITY MEASURING DEVICE (71) Applicant: InterValve, Inc., Minnetonka, MN (US)

(72) Inventors: William J. Drasler, Minnetonka, MN (US); Mark Ungs, Minnetonka, MN (US)

(73) Assignee: InterValve, Inc., Plymouth, MN (US)

( * ) Notice: Subject to any disclaimer, the term of this patent is extended or adjusted under 35 U.S.C. 154(b) by 0 days.

(21) Appl. No.: 14/667,555

(22) Filed: Mar. 24, 2015

(65) Prior Publication Data

US 2015/0196230 A1    Jul. 16, 2015

Related U.S. Application Data

(63) Continuation of application No. 13/766,464, filed on Feb. 13, 2013, now Pat. No. 8,998,827.

(60) Provisional application No. 61/598,085, filed on Feb. 13, 2012.

(51) Int. Cl.
*A61B 5/107* (2006.01)
*A61B 19/00* (2006.01)
*A61F 2/24* (2006.01)
*A61M 25/01* (2006.01)
*A61M 25/10* (2013.01)

(52) U.S. Cl.
CPC ........... *A61B 5/1076* (2013.01); *A61B 19/5244* (2013.01); *A61F 2/2496* (2013.01); *A61M 25/0108* (2013.01); *A61M 25/1002* (2013.01); *A61B 2019/5236* (2013.01); *A61B 2019/5238* (2013.01); *A61B 2019/5276* (2013.01); *A61B 2019/5466* (2013.01)

(58) Field of Classification Search
CPC . A61M 29/02; A61M 25/10; A61M 25/1002; A61M 25/0105; A61M 25/0108; A61M 2025/1059; A61M 2025/1079; A61M 2025/1086; A61B 6/12; A61B 2017/00783; A61B 2019/5466; A61B 5/1076
See application file for complete search history.

(56) References Cited

U.S. PATENT DOCUMENTS

| 5,908,448 | A | 6/1999 | Roberts et al. |
| 7,195,612 | B2 | 3/2007 | van Sloten et al. |
| 7,951,111 | B2 | 5/2011 | Drasler et al. |
| 8,406,867 | B2 | 3/2013 | Kassab |

(Continued)

OTHER PUBLICATIONS

United States Patent and Trademark Office, Notice of Allowance mailed Dec. 1, 2014 in U.S. Appl. No. 13/766,464, 5 pages.

(Continued)

*Primary Examiner* — Max Hindenburg
(74) *Attorney, Agent, or Firm* — Inskeep IP Group, Inc.

(57) ABSTRACT

A balloon catheter is used for dilating tubular members of the body such as dilating stenotic aortic valve leaflets found in the aortic root, and measuring the shape and dimensions of the annulus. The balloon has two larger diameter bulbous regions; one is positioned in the left ventricular outflow tract (LVOT) and the other in the aortic sinus; a smaller diameter waist region is positioned across the aortic annulus. During inflation of the balloon, the balloon waist expands in diameter until it comes into contact with the aortic annulus. The balloon pressure and inflation volume is monitored during inflation so that an inflection point in the dP/dV curve is seen at the point of contact of the waist with the annulus. Radiopaque rings and/or marker bands in the device allow the size and orientation of the elliptical annulus to be calculated.

7 Claims, 8 Drawing Sheets

(56) References Cited

U.S. PATENT DOCUMENTS 8,469,989 B2 6/2013 Schaeffer et al.
8,608,789 B2 12/2013 Konstantino et al.
8,637,132 B2 1/2014 Bavaro et al.

OTHER PUBLICATIONS

United States Patent and Trademark Office, Final Office Action mailed Sep. 24, 2014 in U.S. Appl. No. 13/766,464, 5 pages.
United States Patent and Trademark Office, Office Action mailed Apr. 8, 2014 in U.S. Appl. No. 13/766,464, 7 pages.

ELLIPTICITY MEASURING DEVICE

RELATED APPLICATIONS

This application is a continuation of U.S. patent application Ser. No. 13/766,464 filed Feb. 13, 2013 entitled Ellipticity Measuring Device, which claims priority to U.S. Provisional Application Ser. No. 61/598,085 filed Feb. 13, 2012 entitled Ellipticity Measuring Device, both of which are hereby incorporated herein by reference in their entireties.

FIELD OF THE INVENTION

This invention is related to balloon catheters used for locating a position within a blood vessel or tubular member of the body, dilating tissue found within the tubular member, and measuring the diameter, the perimeter, or the elliptical index of the tissue or the tubular member. Specifically, this device is intended for locating the balloon across the aortic annulus and aortic sinus, dilating the diseased aortic valve leaflets, and measuring the ellipticity, perimeter, or diameter characteristics of the annulus or sinus region.

BACKGROUND

This patent application makes reference to and thereby incorporates all information found in U.S. patent application Ser. No. 10/856,494 (now issued U.S. Pat. No. 7,618,432) and Ser. No. 10/846,613 (now issued U.S. Pat. No. 7,744,620) by Wesley Pedersen et al., particularly information found in the specification and drawings related to FIGS. 5A-5L. Also, this patent application makes reference to and thereby fully incorporates all information found in issued U.S. Pat. No. 7,951,111 and U.S. patent application Ser. No. 13/108,938 by William J. Drasler et al.

Currently cylindrically shaped balloons are used to perform valvuloplasty procedures wherein the stenotic aortic valve leaflets are dilated or pushed back into the space of the aortic sinus. This procedure is typically performed under fluoroscopic guidance while the heart is beating. Movement of the heart, flow of blood, and inaccuracies in fluoroscopic guidance do not allow for accurate placement of the valvuloplasty catheter across the aortic annulus and sinus.

Recently dogbone-shaped balloons have been presented (see U.S. patent application Ser. No. 10/856,494 by Wesley Pedersen) that provides for improved positioning across the aortic annulus and sinus. Also, dogbone-shaped balloons have been presented that are able to measure the diameter of the aortic annulus as well as indicate the compliance characteristics of the aortic annulus (see William J. Drasler, U.S. Pat. No. 7,951,111).

Transcatheter aortic valve implantation (TAVI) is currently being adopted as a method to treat stenotic aortic valve disease. In this procedure a stented aortic valve is placed across the aortic valve annulus and into the aortic sinus region to hold back the diseased native valve leaflets. The stent portion of these valves tends to have a round cross-sectional shape. The annulus, however, tends to have an oval or elliptical shape owing to its anatomical location between the pulmonary valve and the mitral valve. Placement of a round stent into the elliptical opening of the annulus tends to form a leak pathway for blood around the implanted valve at each end of the major axis of the elliptically shaped annulus.

In some instances the elliptical shape of the annulus is reformed into a circular shape with a specific diameter and perimeter as the TAVI device is implanted. For these patients whose annulus can be reformed, it is beneficial to know the dimensions of the annulus in a stretched condition such that a properly sized TAVI device can be implanted without leakage of blood and without causing dissection of the annulus. For those patients that have a more calcified or less compliant elliptical annulus, it would be beneficial for the physician to know under what level of pressure the elliptical will reform to a round shape, or alternately, if that patient is perhaps not a suitable candidate for a TAVI device.

SUMMARY

The present invention is a balloon catheter used for dilating tubular members of the body such as dilating stenotic aortic valve leaflets found in the aortic root, and measuring the shape and dimensions of the annulus. The balloon has two larger diameter bulbous regions; one is positioned in the left ventricular outflow tract (LVOT) and the other in the aortic sinus; a smaller diameter waist region is positioned across the aortic annulus. During inflation of the balloon, the balloon waist expands in diameter until it comes into contact with the aortic annulus. The balloon pressure and inflation volume is monitored during inflation so that an inflection point in the dP/dV curve is seen at the point of contact of the waist with the annulus.

Emb 1

Variable Waist and Variable Bulb Ring

A circular variable ring of radiopaque (ro) marker dots or deposits (for example) located around the circumference of the balloon waist can be observed under fluoroscopy to determine the perimeter of the annulus, its elliptical index (EI), and the appropriate size of TAVI device to implant into the patient. The spacing between the ro marker dots can be set to a known dimension or a specified number of dots can be placed around a perimeter of the balloon waist or bulb. The ro markers described in this invention can alternately be ultrasound markers, MRI markers, electromagnetic signal generators (such as small coils), or other means that are detectable via an energy means other than fluoroscopy that is capable of penetrating its signal through human tissue.

An additional variable ring of ro markers can be placed around the distal bulb of the balloon; the variable ring can change in its diameter or perimeter. Since this portion of the balloon is located in the LVOT, it will assume a circular cross-section when it is placed under pressure. The shape of the ring of bulb markers under fluoroscopy will be determined by the angle, theta, of x-ray beam with respect to the z-axis of the catheter. For most fluoroscopic views the shape will assume that of an ellipse with theta equal to arc cos (major axis/minor axis). The size of the viewed ellipse can be influenced by magnification which is affected by the distance of the object of interest from the energy source and from the collector means. With the angle, theta, known, one can then determine the elliptical index (i.e., ratio of major axis to minor axis) of the annulus. Thus, one can measure the ratio of major to minor axes of the annulus ellipse and calculate the elliptical index, EI, of the annulus by examining a balloon having one portion with an RO ring that is known to be round and another portion with an RO ring in an area of interest and that can be used to measure its EI. This EI information can be determined from only a single fluoroscopic image. Although the size of the ellipse is influenced by a magnification factor, the EI measurements for the annulus via the bulb ring are relatively accurate and not significantly influenced by magnification, as long as the bulb ring is within 1-4 cm of the waist ring.

Emb 2

Waist and Bulb Ring Plus Shaft Markers

In an alternate embodiment one can measure the absolute dimension for the waist by using linear ro markers placed along a linear span of the shaft beneath the balloon waist along the guidewire tubing. The angle, theta, is known from measurement of the ratio of the major and minor axes of the bulb ro markers, minor axis/major axis=cos(theta). The length between marker bands can be used to determine the absolute dimensions and absolute shape of the annulus. The unmagnified length or span for the linear span of ro markers is found from the angle theta as: unmagnified span=actual span(sin(theta)). The magnification factor is then determined by Magnification factor=measured linear span/unmagnified linear span.

Emb 3

Waist and Absolute Bulb Ring

In still another embodiment the ring of ro markers found on the distal bulb of the balloon is formed such that the diameter of the ring is a fixed and known diameter. This can be accomplished via several of the manufacturing methods described in the prior art referenced in this application. For example, a less compliant material can be placed around the bulb region of the balloon. Upon examination of the shape of the circular bulb markers under fluoroscopy, the length of the major axis of the image will be reflective of the actual diameter of the circular ring. The minor axis will be equal to the major axis length multiplied by cos(theta). A fixed spacing between ro deposits around the balloon perimeter can assist in determining local dimensions of the waist or bulb.

The magnification effect that can occur when viewing an x-ray or fluoroscopic image is generally proportional to the distance between the object being imaged and the collector device that receives the x-ray or other energy stream or means. Magnification of the fluoroscopic signal can affect the length of a linear span of ro markers as viewed on its fluoroscopic image; the use of a fixed ro ring of ro markers, however, is not affected by magnification affects since the major axis as viewed in the fluoroscopic image is a correct interpretation of the fixed circular diameter of the ro ring. Generally, the location of the bulb ring is close enough to the waist ring such that this difference does not produce a significant error in the magnification, (i.e., the error is less than 1 mm).

Emb 4

Bulb Rings and a Waist Ring

In yet another embodiment the balloon can be formed with fixed ro marker rings around each of the bulbs and an expandable of variable ring around the waist. The actual dimension for the waist and annulus would be an average of the dimensions as identified by an average of two absolute measurements of two RO rings that are located both closer to and farther from the collector device by an equal amount. The centrally located waist between the two bulb ro marker rings then allows the magnification to be addressed by using an average dimension for the bulb ring diameters as viewed on the fluoroscopy images.

Emb 5

Multiple Images with Waist Ring and Shaft Markers

In yet further another embodiment the balloon having a waist ring and shaft markers is located across the annulus. A fluoroscopic image is taken and the ratio of linear span as observed with respect to the actual linear span of the shaft markers. A second image is taken by rotating the image camera through an angle, phi, along a second axis for the x-ray camera. The second fluoroscopic image will have a different ratio for the observed length/actual length for a linear span of ro markers. The fluoroscopic image will also be rotated in the image plane by an angle, beta. There is only one true location for the z-axis of the catheter and the position of the object of interest, i.e., the fixed or variable span of ro markers that allows a measurement of two different length ratios and two magnification factors after the camera has been rotated a known number of degrees.

Once the shaft direction is known, and the magnification is known for the object of interest, the camera can be positioned such that it projects an image in any desired view. For example, the balloon can be observed in a plane that is perpendicular to the shaft. Rotating the camera around the shaft, around the z-axis, can provide multiple images of the annulus as viewed from around the catheter shaft. Such images can provide relative or absolute dimensions of the major and minor axes of the elliptical annulus (via view of the waist ring) along with all other images located in between. Alternately, positioning the camera to view directly down the z-axis of the catheter will allow visualization of the waist ring directly with one view. A catheter with an absolute bulb ring diameter would provide the absolute dimensions for the elliptical annulus. A catheter with a variable bulb ring will provide relative dimensions of the elliptical annulus and can be used to identify an ellipticity index, EI.

Additionally, the camera could be repositioned at an oblique angle with respect to the axis with a specific known angle, theta, and with a specifically known magnification. The major axis of the round fixed ro ring as seen on fluoroscopy can define an x-axis, and the length of the major axis is equal to the diameter of the fixed ring ro span; the fluoroscopic view of the waist in a similar x-direction will have an accurate dimension, using the fixed ro ring as a basis. The dimension of the image of the waist ring in a y-direction perpendicular to the x-direction will have dimensions that have been reduced by a factor of cos(theta). The major and minor axes of the annulus ellipse can be determined by vector components in the x-axis and adjusted y-axis components.

The balloon waist is formed from a semi-compliant (sc) material that is able to stretch under pressure until it comes into contact with the annulus as the balloon is being inflated. During inflation, the balloon pressure and inflation volume is monitored such that during contact of the waist with the aortic annulus an inflection point is observed in the dP/dV curve. At the point of contact fluoroscopy, ultrasound, RMI, electromagnetic signaling, or other means can be used to examine the image and determine the shape of the annulus, its EI, and in some embodiments determine its absolute dimensions.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is a catheter with a balloon located at the distal portion for transcutaneous delivery into a tubular member of the body and more specifically it can be used during the TAVI procedure. A region of the balloon provides information concerning the shape and size of the tubular member such as the annulus or the aortic sinus. Another region of the balloon can be used to dilate diseased leaflets of the aortic valve. The balloon can in some embodiments be used to identify a relative shape of the annulus and in other embodiments it can provide absolute dimensions for the annulus or aortic sinus region.

Figure 1:
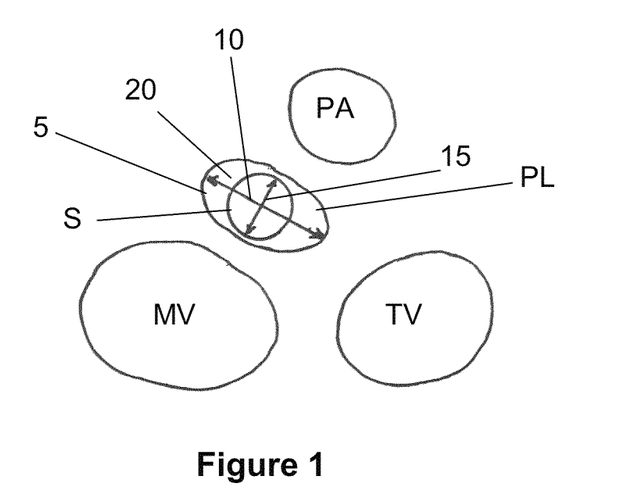
FIG. 1 is a top cross sectional view of an aortic annulus.

The shape of the aortic annulus 5 is generally elliptical or oval in a cross-sectional view as shown in FIG. 1. The aortic annulus 5 is located between the pulmonary artery, PA, the mitral valve annulus, MV, and the tricuspid valve, TV. Generally, the major axis 10 extends along the mitral valve portion of the aortic annulus 5. The minor axis 15 of the annulus 5 is directed perpendicular to the major axis 10. When a stented valve used for the TAVI procedure is implanted across the elliptical annulus, it can form a perivalvular leak 20 these leaks tend to occur at the ends of the major axis 10. Perivalvular leaks 20 are exacerbated by the presence of calcium nodules.

Figure 2:
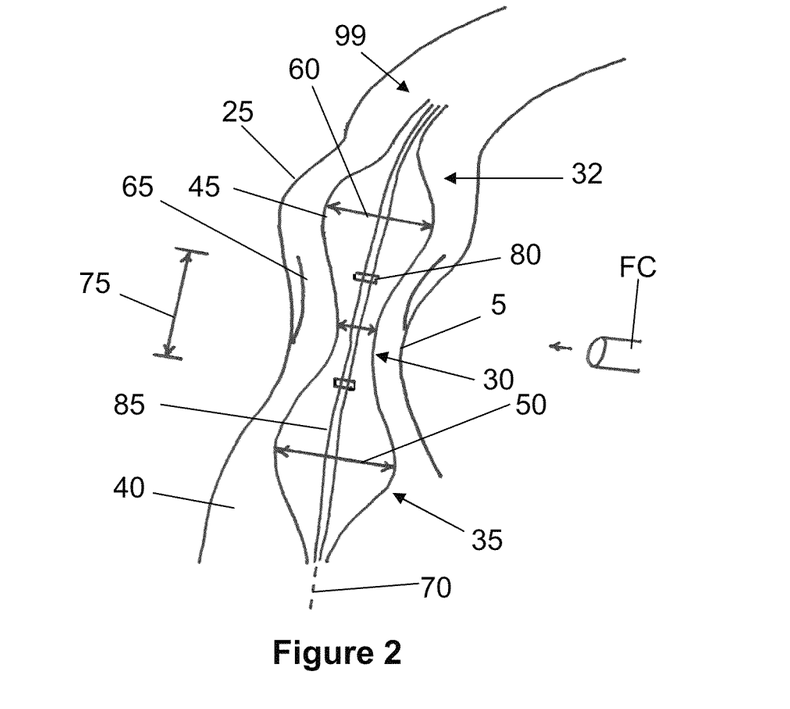
FIG. 2 is a cross sectional view of a balloon catheter within an aortic valve according to the present invention.

A view of the annulus 5 and aortic sinus region 25 via a longitudinal section is shown in FIG. 2. The aortic annulus 5 is shown as the narrowest region after the diseased leaflets 65 have been pushed aside into the aortic sinus region 25. The waist 30 of the balloon 32 of the present invention forms the narrowest region of the balloon and is intended to be positioned adjacent to the aortic annulus 5. The waist 30 is intended to stretch outwardly under increasing balloon pressure to place the waist into contact with the elliptically shaped annulus along its entire perimeter. The distal bulb 35 forms another region of the balloon 32 that is positioned in the left ventricular outflow tract, LVOT 40. The proximal bulb 45 forms another balloon region that is positioned in the aortic sinus 25. It is the proximal bulb 45 that is responsible for dilating the diseased native leaflets 65 outwards into the AS region.

As the balloon 32 is inflated, the distal bulb 35 is able to expand outwardly without significant restriction from adjacent tissues and hence will assume a round cross-sectional shape. The material of construction for the distal bulb region can be semi-compliant (sc) or noncompliant (nc) polymeric material. The sc material option for the distal bulb 35 does not have the larger compliance associated with the sc waist region 55. The distal bulb region 35 of the balloon 32 is larger in diameter than the waist diameter 55 and the aortic annulus 5 and serves to hold the balloon 32 in position such that it cannot move toward the aorta. The distal bulb 35 should have a larger perimeter than the perimeter of the annulus 5; for example the proximal bulb diameter 60 of the proximal bulb should be 1-7 mm larger than the effective diameter of the annulus 5 (the diameter of a circle with the same perimeter as the annulus 5). The sc material for the distal bulb 35, for example, can be nylon or other polymer that has substantially reached its maximum diameter at a pressure of 3-4 atm. For a nc distal bulb 35, a PET, nylon, or fiber wrap can be used to reduce the amount of compliance found in the distal bulb 35. A nc distal bulb 35 should dilate or stretch in diameter less than 1-3% for a pressure of 1-4 atm to provide a known fixed diameter with 1 mm accuracy or better. A sc distal balloon region can expand approximately 3-6% for a pressure increase from 1-4 atm. Other processing methods can be used as described in the earlier referenced patents.

The proximal bulb 45 is similarly formed from sc or nc material as described for the distal bulb. The proximal bulb 45 is also larger, when inflated, than the waist 30 or annulus 5. The proximal bulb 45 serves to dilate the leaflets 65 outwards as well as prevent the balloon 32 from migrating under pressure back into the left ventricle. Contact of the proximal bulb 45 with the valve leaflets 65 occurs at low pressures of 0-2 atm and generally pushes the leaflets back into the aortic sinus region 25 upon reaching a pressure of 2 atm. The proximal bulb 45 is sized to not allow the 25, including the volume of the diseased leaflets 65, to dissect upon inflation to a pressure of up to 4 atm.

The waist 30 is formed from a sc material that is more compliant than either the distal bulb 35 or proximal bulb 45. The waist 30 should be able to expand up to 4-5 mm in diameter when the pressure increases from approximately 2 to 4 atm. It can be formed, for example of a polyurethane, nylon, or other sc material. The material for the waist 30 can be an elastomeric material such as silicone or other cross-linked polymer. The waist 30 can be formed from the same material as the bulbs but can be processed such that it is able to expand outwards from a smaller diameter to a larger diameter as the pressure is increased from 0-4 atm; the diameter of the waist always being smaller than that of the bulbs, even at 4 atm. Under low pressures of approximately 0-2 atm the waist 30 expands via an extension deformation but has not made contact with the annulus 5. Thus the waist 30 is sized such that its perimeter or effective diameter (of a circle with the same perimeter as an oval) is smaller than the annulus perimeter at less than 2 atm. The waist 30 must expand to reach and contact the annulus diameter that could be 4-5 mm larger than its lower pressure diameter at approximately 2 atm or below.

As the waist 30 expands in diameter under increasing inflation pressure or inflation volume, the perimeter of the waist 30 comes into contact with the perimeter of the annulus 5. At this contact point, an inflection is observed in the dP/dV curve for the balloon. This inflection point generally occurs at a pressure of approximately 2-3.5 atm; the inflection occurs after the leaflets 65 have been pushed aside. At a balloon pressure of approximately 2 atm the waist 30 will have a generally ridged circular cross section and will try to force the elliptical annulus 5 into a circular shape. At the contact point, the outward force exerted by the waist 30 onto the annulus 5 is zero. Further balloon pressure can be applied to further induce the annulus 5 to form a round shape by enlarging the waist 30 and forcing it into a round shape at higher pressures. If the waist 30 of the balloon 32 remains elliptical, it is one purpose of one embodiment of the present invention to identify the ellipticity index, EI, for the annulus; the EI is the ratio of the major axis 10 to minor axis 15 of the ellipse. In another embodiment, the present invention will provide information regarding the pressure required to form the elliptically shaped annulus 5 into a circular shape. In another embodiment, the dimensions of the annulus 5 will be absolutely measured and reported to the operator to allow proper selection of the appropriate size of TAVI device to implant.

In one embodiment, as shown in FIG. 2, the catheter 99 of the present invention is injected with a contrast medium that can be visualized under fluoroscopy. The fluoroscopy camera, FC, can be oriented such that it directs x-rays in a direction perpendicular (i.e., theta=90 deg) to the axis 70 of the catheter 99. This perpendicular orientation can be accomplished by monitoring the fixed linear span 75 between two marker bands 80 located within the balloon 32 along the guidewire tubing 85 at two or more oblique orientations (with respect to the catheter axis) of the camera around the perimeter of the balloon. Also, the diameter of the linear span as observed in the fluoroscopy plane will be measured. Geometrical considerations regarding the length of the fixed span with respect to the camera orientation and rotation of the image of the linear span (as well as its altered displacement) allow a determination of the catheter axis 70 orientation and position of the object of interest (i.e., the linear span of ro markers or the aortic annulus, for example) to be known in 3D space. Only one axis location in 3D space will be consistent with the two lengths of the fixed span and its rotation in the fluoroscopic image plane at two different orientations of the camera with respect to the catheter axis. Once the axis orientation is known, along with the position of the object of interest, the camera can then be placed, for example, perpendicular to this catheter axis, or at another angle. Rotating the camera, for example, around the catheter axis by 180 degrees, while observing the diameter of the waist under fluoroscopy at several (perhaps 2-8 distinct positions) camera orientations, will allow a determination of the ellipticity index, EI, of the annulus to be observed, measured, and identified. Alternately, the camera can be placed to view along the z-axis 70 of the catheter 99 or at any oblique angle with respect to the z-axis 70 of the catheter 99.

Figure 3:
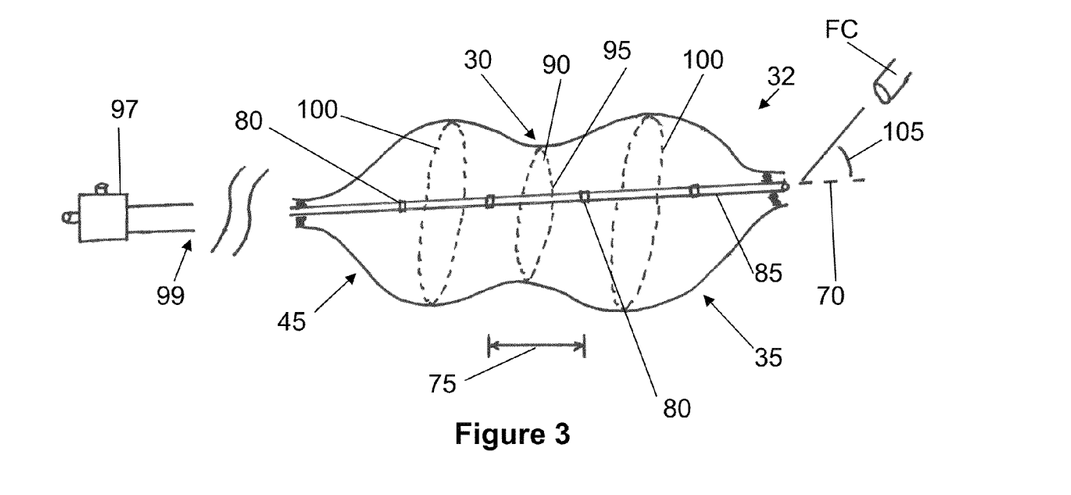
FIG. 3 is a cross sectional side view of a balloon catheter according to the present invention.

FIG. 3 shows an embodiment of the present invention having a balloon 32 with distal bulb 35, a proximal bulb 45, and a waist region 30. In one embodiment, the balloon 32 has a circular waist variable ring 90 of radiopaque (ro) deposits 95 placed around the waist 30; the variable waist ring 90 is able to stretch or vary its perimeter since the deposits are not continuous but are instead discrete deposits separated by a space between individual ro deposits. The space between individual deposits can be controlled if desired such that the spacing can be used to contribute as a basis for determining the absolute dimensions of a waist ring or annulus. The ro deposits can be formed from tungsten or other ro material used in the art for ro markers, and can be applied to the outside of the balloon via a liquid dispersion such as an ink or as a stamping process. The ro deposit 95 can be covered by a secondary coating step to ensure that the ro deposit does not embolize. Alternately, the ro deposits can be applied via any other suitable process including plasma deposition, or trapping ro deposit material between two layers of polymer such as two layers of balloon material. The proximal bulb or the balloon is located nearest to the manifold 97 of the catheter 99.

In addition to the variable ring 90 located in the waist, one embodiment has an additional ring 100 of ro deposits located around a circumference of the distal bulb 35. The ring 100 can be a variable ring as shown in FIG. 3 or it can be a fixed ring or a fixed span (i.e., having a fixed diameter, perimeter, or span) as shown in later figures and embodiments. The distal bulb 35 is not restricted by surrounding tissue and can expand freely under pressure. The variable ring located in the distal bulb region thereby forms a round shape when the balloon 32 is inflated to a pressure of 1-4 atm. Observation under fluoroscopy of the minor axis (i.e., the smaller viewed axis) of the round variable ring 100 will accurately identify the plane that contains the fluoroscopy camera direction and the z-axis 70 of the catheter 99. Observation and measurement of the major axis of the round variable ring 90 provides both a direct measurement of the angle 105, theta, between the fluoroscopy camera and the z-axis 70 of the catheter, where theta=arc cos (minor axis/major axis). Once the angle 105, theta, between the camera FC and the catheter axis 70 is known, the ellipticity index, EI, for the annulus can then be determined. The length the ellipse as identified by the variable waist ring 90 in the direction of the major axis of the distal bulb ring major axis is absolute and can be measured directly using the major axis of the distal bulb ring as a basis. The length of the ellipse in the direction of the minor axis of the distal bulb ring minor axis is measured directly using the minor axis of the distal bulb ring as a basis (the minor axis of the ellipse can be measured directly and corrected by a factor of 1/cos(theta) and then using the distal bulb major axis as a basis). Each element of the annular ellipse can similarly be determined by breaking down its vectors into one that is parallel with the major axis of the distal bulb ring and parallel with the minor axis of the distal bulb ring 35. Hence, the major and minor axis of the annular ellipse can be determined by using the distal bulb ring for establishing a coordinate system within the cross-section of the balloon and using the distal bulb as a basis for determining relative dimensions for the major and minor axes for the annular ellipse. The ellipticity index, EI, can then be calculated for the annulus, where EI=major axis/minor axis.

Variable Waist Ring and Fixed Bulb Ring

Figure 4:
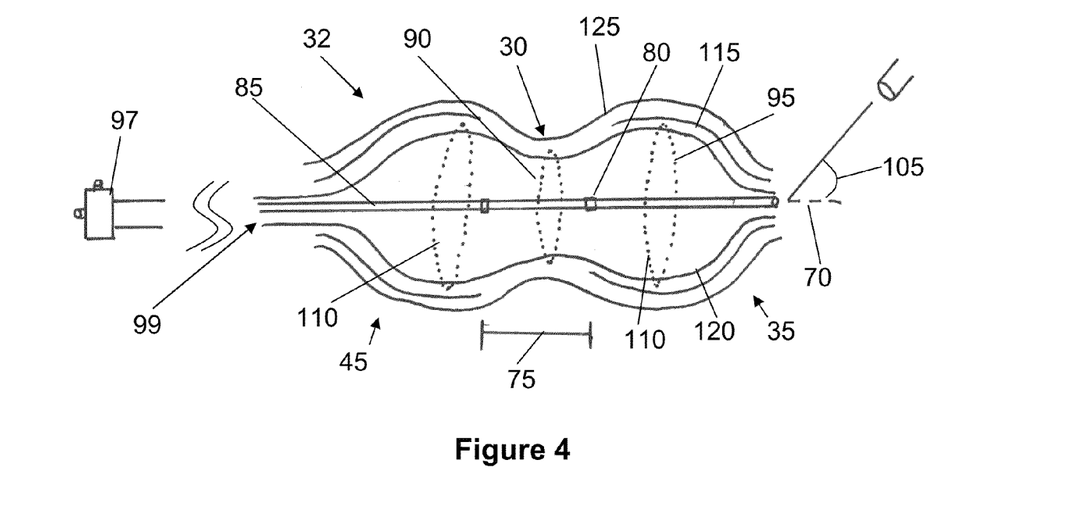
FIG. 4 is a cross sectional side view of a balloon catheter according to the present invention.

In yet another embodiment shown in FIG. 4 the distal bulb 35 can have a fixed bulb ring 110 of ro markers 95 or a fixed span 75 of markers that have a fixed and known diameter or perimeter. In this embodiment the distal bulb 35 is formed from a nc material. As shown in FIG. 4, an outer wrap 115 can be place around the distal bulb 35 of an inner balloon 120 to form a nc distal bulb. The fixed bulb ring 110 can be placed between two layers, for example, between the outer wrap 125 and the inner balloon 120 to ensure that the ro deposits 95 cannot embolize. An outer coating of polymeric material 125 can be applied to the outside of the entire balloon 32, if desired, to coat over the ro deposits 95 to ensure that they do not embolize; a flexible polyurethane coating of less than 0.001 inch, for example, could be applied for this purpose.

This balloon 32 with a variable waist ring 90 and fixed bulb ring 110 functions in a similar manner to the embodiment with the variable distal bulb ring. The distal bulb ring in this embodiment will expand under pressure to form a round shape with a known diameter. Measurement of the major axis of the distal bulb ring under fluoroscopy will provide an exact basis from which to compare the measurements made in the annular ellipse. The minor axis of the distal bulb under fluoroscopy can provide a basis for measuring the annulus (i.e., the waist fixed ring) in a direction parallel with the minor axis of the distal bulb. With this embodiment, the specific accurate dimensioning of the annulus can be determined with a single fluoroscopic image from an oblique orientation of the x-ray camera FC with respect to the z-axis 70 of the catheter 99. Other elements of the balloon bear reference numerals similar to those described in other embodiments.

Variable Bulb Ring and Linear Fixed Span

In another embodiment the distal portion 35 of the catheter 99 has a guidewire tubing 85 that extends through the balloon 32. In addition to the variable ring located in the waist 30, marker bands 80 can be placed along the guidewire tubing 85 to form a fixed linear span of ro markers; the markers 80 are fixed at a specific and known distance or span. The distance between two fixed span markers 80 is a function of the ratio of the observed linear span to the actual length of the linear span. As described earlier, two fluoroscopic images taken of the catheter will provide a different effective length or span between the fixed span markers 80. The two fluoroscopic images will also allow the angle of rotation of the fluoroscopic image as well as its position to change. Information from the two fluoroscopic images are used to determine the location of the z-axis 70 in 3D space as well as the location of the object of interest (i.e., this is equivalent to knowing the magnification for each of the positions). Only one position of the z-axis 70 in 3D space can exist that satisfies the two observations for the two camera orientations. The magnification factor of the image is proportional to: (the distance from the x-ray emitter to the collector)/distance from emitter to object of interest).

Once the z-axis 70 and the position of the object of interest has been located in 3D space, images of the waist variable ring or ro ring can be taken from a known camera angle with respect to the z-axis 70. The ellipticity of the variable waist ring can then be determined using the fixed linear span of ro markers 80 along the guidewire tubing as a basis, where sin(theta)=(observed linear span/actual linear span)(magnification factor). The plane that contains the x-ray projection and the z-axis 70 will define the y-axis of the coordinate system that is perpendicular to the z-axis; the x-axis being perpendicular to both the x and z axes. The dimensions of the annulus ellipse in the x-axis is measured directly and uses the fixed linear span corrected by the magnification factor and the y-axis is measured directly and adjusted by factor (1/cos (theta)) (magnification factor) and uses the fixed linear span as a basis.

Waist Ring and Two Bulb Rings

In still another embodiment, as shown in FIGS. 3 and 4, the proximal bulb 45 can have a variable ro ring 100 or fixed ro ring 110. The presence of a ro ring on both the proximal bulb 45 and distal bulb 35 allows the magnification factor associated with the distance between the distal bulb 35 or proximal bulb 45 and the waist 30 to be taken into consideration. Since the waist 30 is located between the proximal bulb 45 and distal bulb 35, the amount of magnification of the bulb with respect to the waist 30 will be larger for one bulb and smaller for the other bulb, thereby allowing an average fixed ro span to be used to calculate absolute dimensions for the annulus ellipse.

Figure 5:
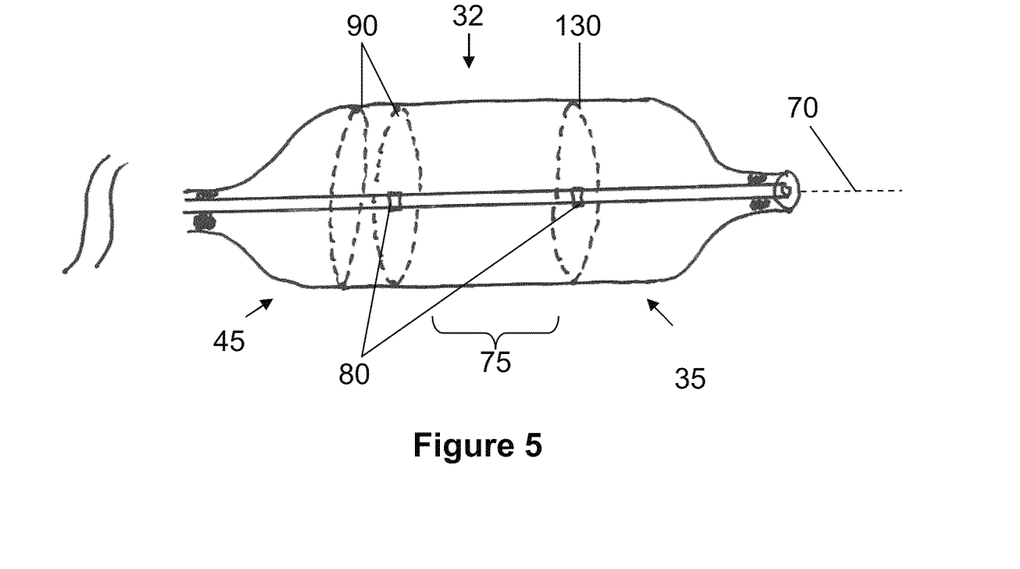
FIG. 5 is a cross sectional side view of a balloon catheter according to the present invention.

In another embodiment shown in FIG. 5 the balloon does not have a bulbous shape but instead it has a cylindrical shape. In this embodiment, a proximal balloon region 45 of the balloon 32 is semi-compliant and has a ro proximal variable ring 90. This ring 90 would be placed adjacent to the annulus. More than one such variable rings 90 can be placed along the proximal sc region 45 of the balloon 32 if necessary to enhance the likelihood that one of the rings 90 is located adjacent to the annulus. A distal balloon region 35 can be sc or nc and has a ro distal ring 130. This ro ring 130 would be placed into the LVOT where enough space exists to allow this region 35 of the balloon 32 to form a circular cross-sectional shape. The ro distal ring 130 can be a variable or fixed ro ring. As described earlier, if the ro distal ring 130 is variable in diameter and perimeter, then only a relative dimensioning of the annulus can be obtained in determining the EI. If the distal ro ring 130 is a fixed ring, then absolute dimensions for the annulus ellipse can be obtained. The construction of the distal region can be accomplished via placement of an outer wrap or an outer coating as described for earlier embodiments.

Figure 6A:
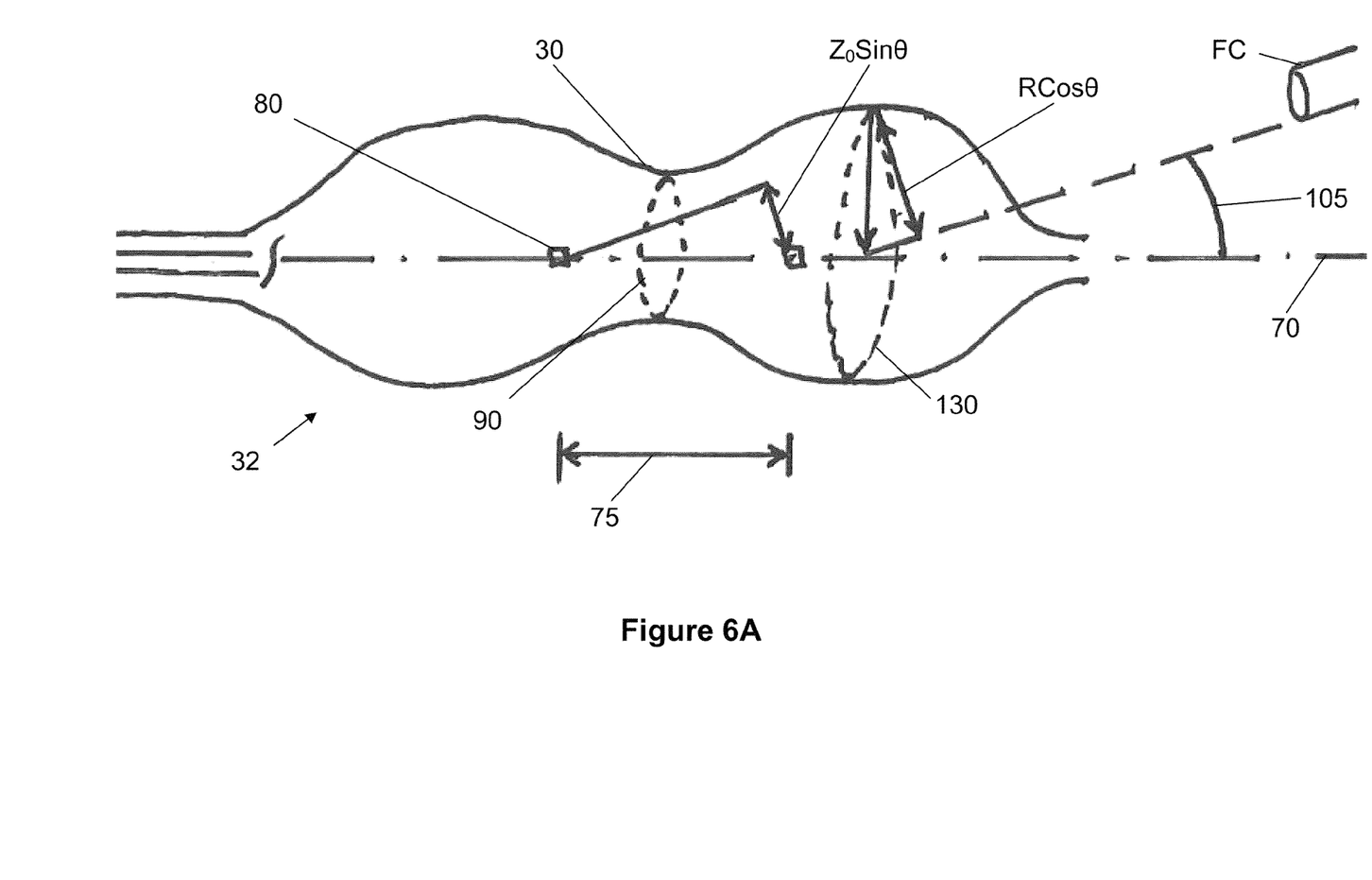
FIG. 6A is a cross sectional side view of a balloon catheter according to the present invention.

To better understand the capability of the present invention the bulbous balloon 32 is shown in FIGS. 6A-6E along with sketches showing the observed images at an angle 105, theta, with respect to the z-axis 70. FIG. 6A shows the balloon having a round distal bulb ring having a fixed bulb ro ring with radius, R. The waist 30 has a waist variable ring 90 of unknown diameter and shape. A fixed linear span of marker bands 80 is located on the guidewire tubing and having a span of Zo units. An x-ray camera, source camera, or fluoroscopy camera, FC, positioned at an angle 105, theta, with respect to the z-axis 70 directs its x-rays toward the balloon 32.

Figure 6B:
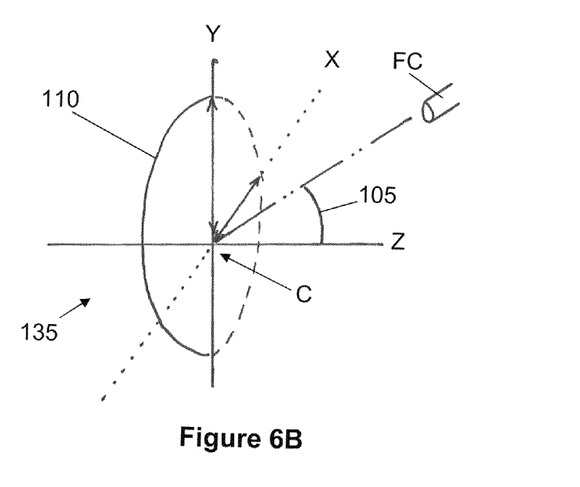
FIGS. 6B-6E are various coordinate systems relating to a balloon catheter according to the present invention.
Figure 6C:
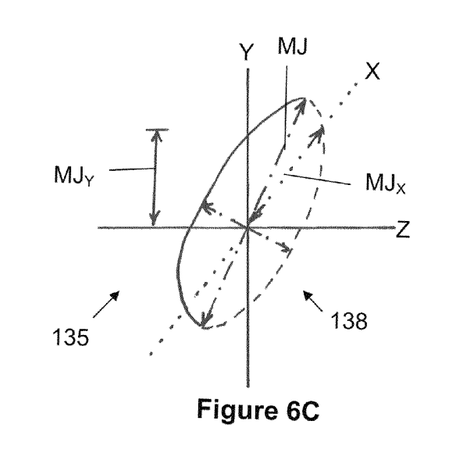
Figure 6D:
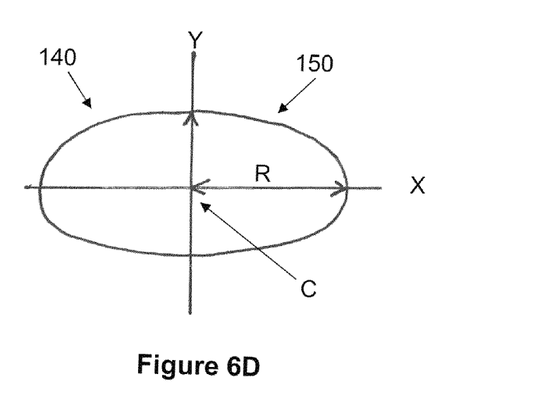

A coordinate system 135 with x and y axes drawn through the fixed distal bulb is shown in FIG. 6B with the center of the circle, C, at the junction of the x and y axes. The x and y coordinate system is drawn through an example actual elliptical waist ring 135 of ro markers in FIG. 6C. The observed shape on fluoroscopy for the fixed bulb ring in the distal bulb is an ellipse 140 as shown in FIG. 6D. The observed shape on fluoroscopy for the example elliptical annulus is an altered ellipse 145 shown in FIG. 6E. The purpose of this exercise is to be able to reconstruct the actual elliptical shape for the annulus based upon the observed shape found for the actually round bulb distal ring 130.

From observation of FIGS. 6A, 6B, and 6D, the effective length for the minor axis, r, of the ellipse observed on fluoroscopy is R cos(theta), where r=R cos(theta). Therefore, by measuring the ratio of r/R one is able to determine theta. The magnitude of the length of the major axis, R, is not affected by the angle 105, theta, and therefore can be used as a basis for determining absolute length for the case of the fixed ring of ro markers. Magnification is not a concern when using a circle or ring of fixed ro markers as long as the waist ring 90 is within a few centimeters of the bulb distal ring 130.

The observed image seen on fluoroscopy for the variable ring 90 found in the waist 30 will be similarly reduced in magnitude in the y-axis by a factor of cos(theta). The x-axis for the fluoroscopic elliptical image of the waist ring (or annulus) as identified in FIG. 6E lies in exactly the same plane and is parallel to the major axis of the ellipse formed by the fluoroscopic image of the distal bulb ring 150 in FIG. 6D.

Figure 6E:
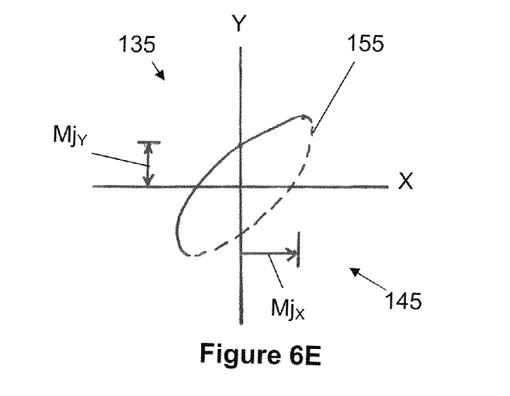

Any component in the x-axis of the observed image in FIG. 6E is an accurate dimension and can be identified using the known basis dimension of the x-axis dimension that is a representation of the circle found in the distal bulb having the fixed diameter ro markers. The component of the observed ellipse in the x-direction, mjx, is the same as the x-component of the actual waist ellipse formed by the waist ring, MJx. Similarly, the component of any point found in the y-axis in the elliptical fluoroscopic image of waist ring 155 of FIG. 6E would be multiplied by a factor (1/cos(theta)) to identify its actual accurate dimension as compared to the known basis dimension found in the distal bulb circle. The component of the observed ellipse in the y-direction, mjy, should be multiplied by a factor 1/cos(theta) to provide the x-component of the actual dimension of the waist ellipse in the x-direction, MJy. The magnitude of the major axis of the actual ellipse formed by the waist ring 155 is a vector sum of MJx and MJy.

Figure 7:
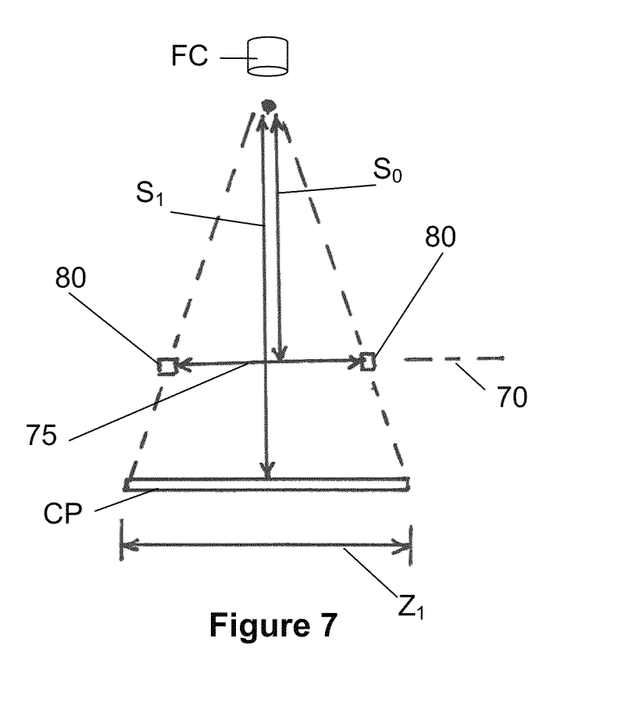
FIG. 7 illustrates calculation of a magnification factor relating to a balloon catheter according to the present invention.

FIG. 7 is intended to describe the magnification factor and the consequences of this additional effect on the accuracy of dimensional and shape analysis. The x-ray camera, source, or fluoroscopic camera, FC, is located at point S. The x-rays tend to fan out as they extend away from the source. In this example the x-rays strike the object of interest (i.e., the ro markers) having a length of Zo and located a distance, S0, away. The collector plate (CP) or image intensifier is located at a distance S1 from the source and received an image signal with a magnified size of Z1. The image that is viewed by fluoroscopy and other means, such as ultrasound, would then be magnified such that Z1=((S1)(Zo)/So).

The balloon waist and each of the bulbs are located within 2-4 cm of each other such that any magnification error associated with using an absolute bulb dimension to determining an annulus dimension will not be large, i.e., less than 1 mm. If one were to use the linear span 75 of ro markers along the guidewire tubing one would have to determine both the angle 150 of the x-ray source with respect to the z-axis 70 as well as the magnification factor associated with its location from the source. To do this will require, as stated earlier, an additional fluoroscopic scan at, for example, two different camera positions or two different distances of the source, S, to the object to establish the location of the object of interest or to establish the magnification and to place the z-axis 70 of the catheter 99 and the object of interest into a known location in 3D space.

Figure 8A:
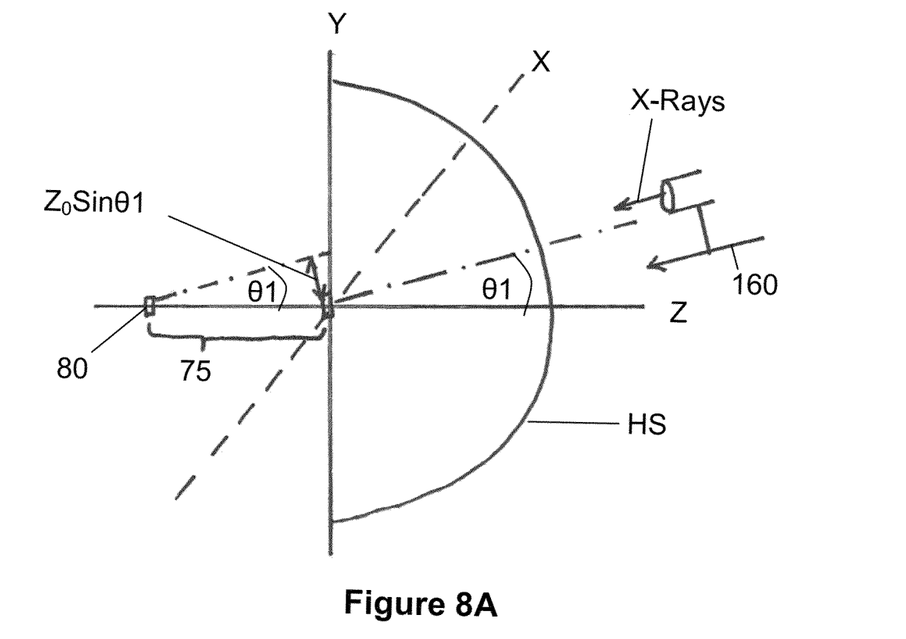
FIGS. 8A-8D are various coordinate systems relating to a balloon catheter according to the present invention.
Figure 8B:
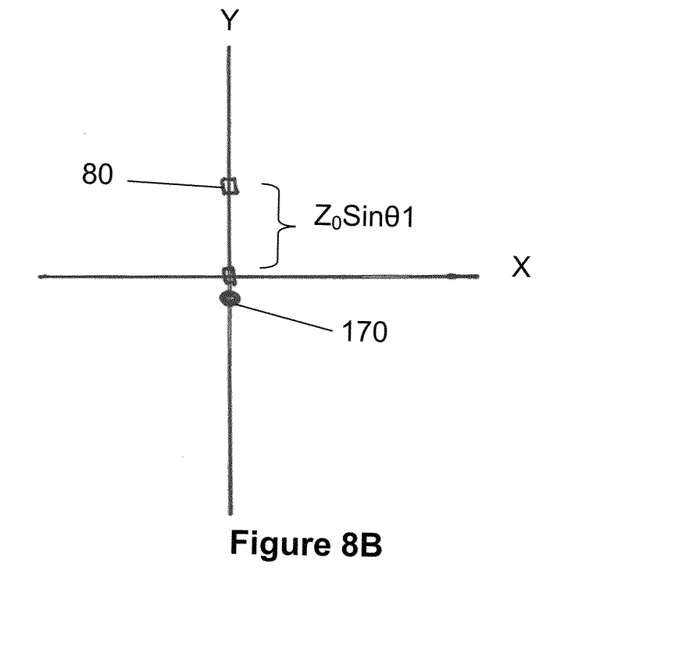

FIGS. 8A-8D are concept drawings that shows the fixed linear span of ro markers with a span of Zo located along the z-axis 70 of the catheter of the present invention. In an example shown in FIG. 8A the x-ray source is directing a stream of x-rays at an angle, theta1, with respect to the catheter axis 70. The x-rays can be directed from anywhere along a surface, for example, of a half sphere, HS, toward the object of interest, the fixed linear span of ro markers or marker bands. The source camera or fluoroscopic camera, FC, can be rotated along a camera axis, (i.e., c-axis 160) with an angle, phi, in the circumferential direction, and the camera is rotated with an arm length, AL, for rotating around the c-axis. The angle of the camera, phi, with respect to its starting position will be arbitrarily set to phi1. As mentioned earlier, the length of the observed linear span via fluoroscopy would be Zo sin(theta1), as shown in FIG. 8B, if the magnification factor was unity. Thus, theta1 is known for a unity magnification. In FIG. 8B, the y-axis for the catheter has been set to align, for example with the direction of the observed image of the linear span.

Figure 8C:
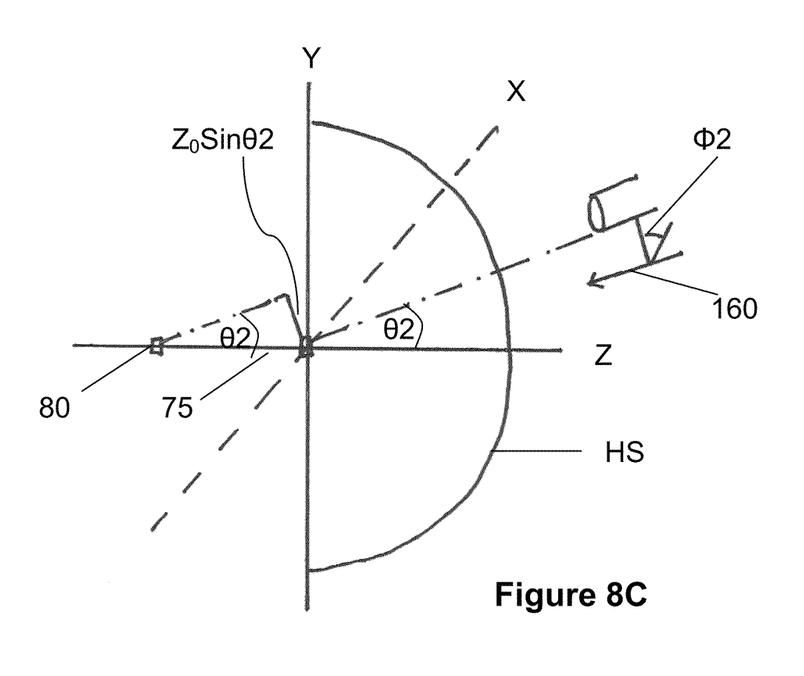
Figure 8D:
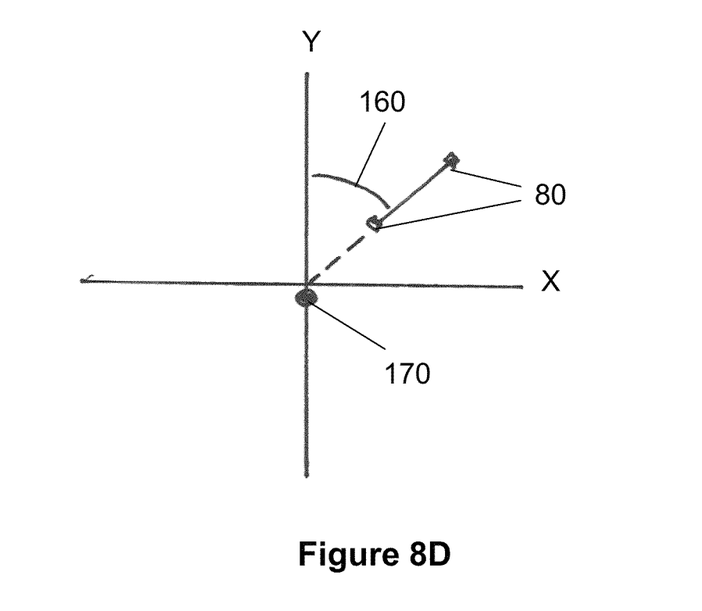

To adequately consider the true magnification (as described in FIG. 8), a second fluoroscopy image is taken by rotating, for example, the camera along its c-axis to a new camera angle of phi2 as shown in FIG. 8C. The x-rays enter the half sphere, HS, at some location that is oblique to the x-, y-, and z-axes. The observed fluoroscopic image of the length of the fixed linear span can be measured as Zo sin(theta2), for a magnification of unity, as shown in FIG. 8D and will be displaced by rotation angle 165, beta, from the y-axis; the y-axis being set by the direction of the first fluoroscopic image as seen in FIG. 8B.

Measurement of the effective length of the linear span of ro markers by movement of an x-ray camera to two different locations allows a solution to two equations with two unknowns. The two equations describing the length of the linear span with respect to the angle of the x-ray onto the z-axis of the catheter and the length of the linear span with respect to its distance from the source and collector (as described by magnification). The information that is measured and known variables include the effective length of the linear span for each of the fluoroscopic images, the rotation angle and absolute position of the camera for the first and second fluoroscopic images, and the rotation angle 165, beta, of the linear fluoroscopic image from the first to second fluoroscopic images, and the displacement of the fluoroscopic image from its initial position or tissue entity, 170, located in a fixed position within the patient. Such tissue entity can be a calcified aortic valve leaflet or other observable tissue member of the body.

Figure 9A:
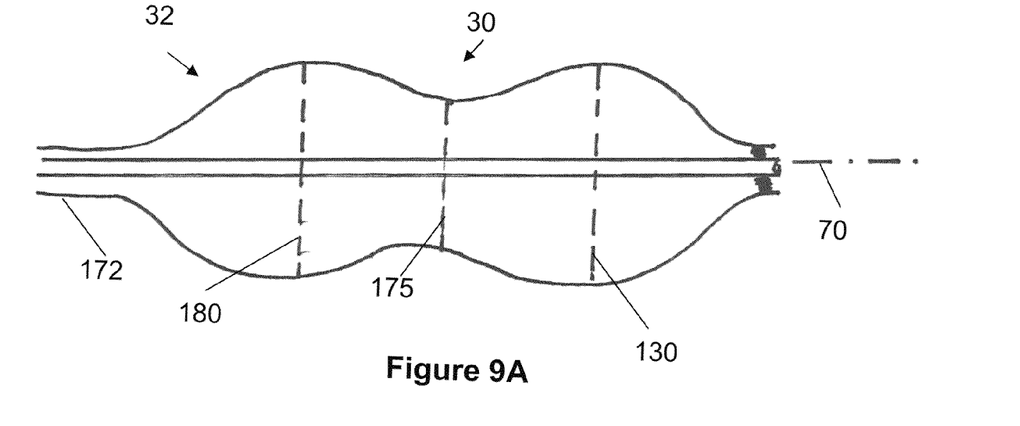
FIG. 9A is a cross sectional side view of a balloon catheter according to the present invention; and, FIG. 9B is a profile cross sectional side view of a balloon catheter according to the present invention.
Figure 9B:
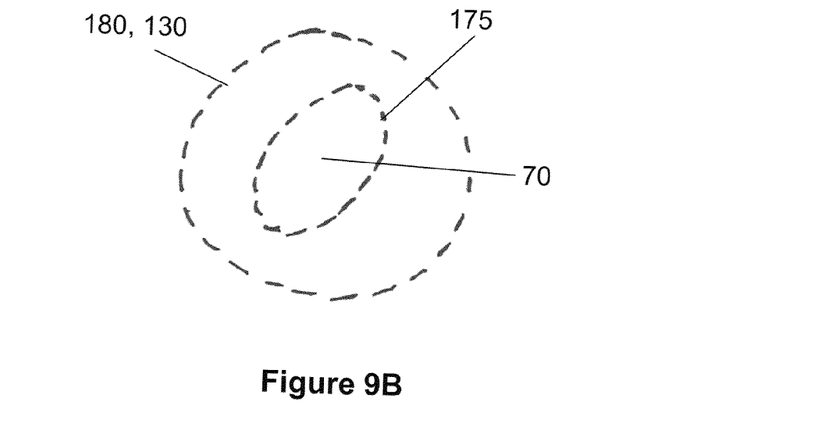

The resulting determination of both the angle of the catheter shaft and the position of the object of interest (or its magnification) in 3D space then allows the fluoroscopy camera, FC, to be placed into a position such that a fluoroscopic view is made either perpendicular to the z-axis of the catheter shaft 172 such as shown in FIG. 9A or in line with the z-axis as shown in FIG. 9B, or at some oblique angle. The perpendicular view allows measurement of the annulus from a longitudinal view of the balloon waist ring 175, with correction for magnification (for absolute dimensions), and this could be performed in several views around the z-axis of the catheter. Also seen are the proximal bulb ring 180 and distal ring 130. The end view as shown in FIG. 9B allows a single view of the elliptical waist ring (or annulus) with a direct reading of the EI from a single view from this direction. Absolute dimensions of the annulus can be determined from consideration of the magnification factor as determined via two prior fluoroscopic images that would place the location of the fixed or variable ro markers in 3D space. Any other oblique view can be taken with the fluoroscopic camera with the knowledge of the location of the z-axis, the location of the ro markers in 3D space, and the location of x-ray camera in 3D space.

It is understood that a patient or organ may move from one fluoroscopic image to the next image. This movement can affect the accuracy of relative or absolute measurements related to dimensions of the annulus or shape of the annulus, including determination of EI. It is therefore understood that identification of a physical entity located within the patient's body can be identified such that the catheter position with respect to this physical entity is monitored and measured during the fluoroscopic procedure. During at least two of the fluoroscopic images, the position of a fixed ro marker, for example, would be located and the distance and angle of position of the ro markers from the physical entity would be measured in a manner similar to that described for the measurement of the linear fixed span of ro markers. Correction can be made for movement of the patient with respect to the fluoroscopy camera, FC, as long as the catheter retains its position with respect to the physical entity. Such physical entity for the case of TAVI procedures could be a calcified valve leaflet or other calcium deposit, for example.

The invention claimed is:

1. A method for determining an axial alignment of an axis of an elongated member of a catheter relative to an axis of a tubular member of the body, said method comprising:
    providing a balloon disposed at a distal end of said elongated member, said balloon having a first semi-compliant region,
    said first semi-compliant region having a first span of radiopaque markers comprising a variable ring of radiopaque markers,
    inflating said balloon to place said variable ring immediately adjacent with the tubular member of the body,
    measuring major and minor diameters of said variable ring via an imaging camera, so as to determine said axial alignment of said axis of said elongated member relative to said axis of the tubular member, said major diameter extending between the furthest portions of said variable ring and said minor diameter extending between the closest portions of said variable ring.

2. The method of claim 1 wherein a spacing between individual radiopaque markers of said variable ring is used to determine said major and minor diameters of said variable ring.

3. The method of claim 1 wherein said elongated member further comprises a second region having a second span of radiopaque markers having a predetermined size,
    measuring said predetermined size of said second span of radiopaque markers via an imaging camera to determine the ovality of said variable ring.

4. The method of claim 3 wherein a spacing between individual radiopaque markers of said second region is used to determine said major and minor diameters of said variable ring.

5. The method of claim 2 wherein said second region is located on a noncompliant region of said balloon and said second span is a fixed ring having said predetermined size.

6. The method of claim 2 wherein said second region is located on a central shaft of said elongated member and said second span is a linear fixed span having said predetermined size.

7. A method for determining an axial alignment and ovality of a tubular member of the body, said method comprising:
    providing a balloon disposed at a distal end of an elongated member, said balloon having a first semi-compliant region,
    said elongated member further comprising a second region located at said distal end of said elongated member,
    said first semi-compliant region having a first span of radiopaque markers comprising a variable ring of radiopaque markers,
    said second region having a second span of radiopaque markers having a predetermined size,
    inflating said balloon to place said variable ring adjacent with the tubular member of the body,
    measuring major and minor diameters of said variable ring via an imaging camera, so as to determine the axial alignment of an axis of said elongated member with an axis of the tubular member; said major diameter extending between furthest portions of said variable ring and said minor diameter extending between closest portions of said variable ring,
    measuring said predetermined size to determine the ovality of said variable ring.

* * * * *